(12) United States Patent
Schostek et al.

(10) Patent No.: US 10,881,454 B2
(45) Date of Patent: Jan. 5, 2021

(54) SURGICAL CUTTER OPERATED WITH DIRECT CURRENT

(71) Applicant: OVESCO ENDOSCOPY AG, Tubingen (DE)

(72) Inventors: Sebastian Schostek, Tubingen (DE); Chi-Nghia Ho, Reutlingen (DE); Michael Melbert, Tubingen (DE); Marc O. Schurr, Tubingen (DE); Thomas Gottwald, Kochel (DE)

(73) Assignee: Ovesco Endoscopy AG

( * ) Notice: Subject to any disclaimer, the term of this patent is extended or adjusted under 35 U.S.C. 154(b) by 666 days.

(21) Appl. No.: 14/774,694

(22) PCT Filed: Mar. 11, 2014

(86) PCT No.: PCT/EP2014/054740
§ 371 (c)(1),
(2) Date: Sep. 10, 2015

(87) PCT Pub. No.: WO2014/140039
PCT Pub. Date: Sep. 18, 2014

(65) Prior Publication Data
US 2016/0022356 A1 Jan. 28, 2016

(30) Foreign Application Priority Data
Mar. 11, 2013 (DE) .......... 10 2013 102 418

(51) Int. Cl.
*A61B 18/14* (2006.01)
*A61B 18/00* (2006.01)
(Continued)

(52) U.S. Cl.
CPC ...... *A61B 18/1447* (2013.01); *A61B 18/1445* (2013.01); *A61B 2018/0072* (2013.01);
(Continued)

(58) Field of Classification Search
CPC ............ A61B 18/1442; A61B 18/1445; A61B 18/085; A61B 2018/126;
(Continued)

(56) References Cited

U.S. PATENT DOCUMENTS 3,354,478 A 11/1967 Allen
3,431,384 A 3/1969 Cooper
(Continued)

FOREIGN PATENT DOCUMENTS

DE 102007003838 A1 8/2008
EP 2392282 A1 12/2011
(Continued)

OTHER PUBLICATIONS

Japanese Patent Office, Notification of Reasons for Rejection, dated Apr. 4, 2017, in application JP 2015-562097.

*Primary Examiner* — Thomas A Giuliani
(74) *Attorney, Agent, or Firm* — RatnerPrestia

(57) ABSTRACT

A minimally invasive surgical implant-cutting instrument of the bipolar type, operated with direct current, with an instrument head which is located at the distal end of an instrument shank, wherein at least two mutually opposing instrument branches, preferably of the linear type, are arranged on the instrument head and between them define a cutting gap for receiving an electrically conductive implant or implant section between them. The electrodes are formed on the mutually facing longitudinal sides of the branches or these are each equipped with at least one electrode, which electrodes are in turn shaped at their mutually facing longitudinal sides to form a cutting edge in order to effect a quasi-linear or punctiform physical contact engagement with the electrically conductive implant or implant section for an electrical short circuit of the mutually opposing electrodes.

18 Claims, 20 Drawing Sheets

(51) Int. Cl.
  *A61B 18/12* (2006.01)
  *A61F 2/04* (2013.01)
  *A61F 2/95* (2013.01)
  *A61B 90/00* (2016.01)

(52) U.S. Cl.
  CPC ............ *A61B 2018/00642* (2013.01); *A61B 2018/00672* (2013.01); *A61B 2018/00678* (2013.01); *A61B 2018/00702* (2013.01); *A61B 2018/00714* (2013.01); *A61B 2018/00761* (2013.01); *A61B 2018/00767* (2013.01); *A61B 2018/00875* (2013.01); *A61B 2018/1266* (2013.01); *A61B 2018/142* (2013.01); *A61B 2090/065* (2016.02); *A61F 2002/044* (2013.01); *A61F 2002/9528* (2013.01)

(58) Field of Classification Search
  CPC .. A61B 2018/00607; A61B 2018/1452; A61B 2018/1266; A61B 2018/142; A61B 17/28; A61B 17/29; A61B 2018/00875; A61F 2002/9528; A61F 2002/30668; A61F 2/95; A61F 2250/0001
  USPC .......... 606/37, 41, 48, 50–52, 108, 205–207
  See application file for complete search history.

(56) References Cited

U.S. PATENT DOCUMENTS

| | | | |
|---|---|---|---|
| 2001/0037109 A1* | 11/2001 | Yamauchi | A61B 18/1442 606/48 |
| 2008/0015575 A1* | 1/2008 | Odom | A61B 18/1445 606/51 |
| 2008/0208193 A1* | 8/2008 | Yamatani | A61B 18/1482 606/48 |
| 2009/0204064 A1 | 8/2009 | Farin et al. | |
| 2010/0087834 A1* | 4/2010 | Eisele | A61B 18/14 606/108 |
| 2012/0265196 A1 | 10/2012 | Turner et al. | |
| 2013/0030428 A1 | 1/2013 | Worrell et al. | |
| 2014/0005667 A1* | 1/2014 | Stulen | A61B 17/320092 606/45 |

FOREIGN PATENT DOCUMENTS

| | | |
|---|---|---|
| JP | 2009514632 A | 4/2009 |
| JP | 2010516361 A | 5/2010 |
| WO | 2007/054321 A2 | 5/2007 |
| WO | 2008/040485 A2 | 4/2008 |
| WO | 2008/090003 A1 | 7/2008 |

* cited by examiner

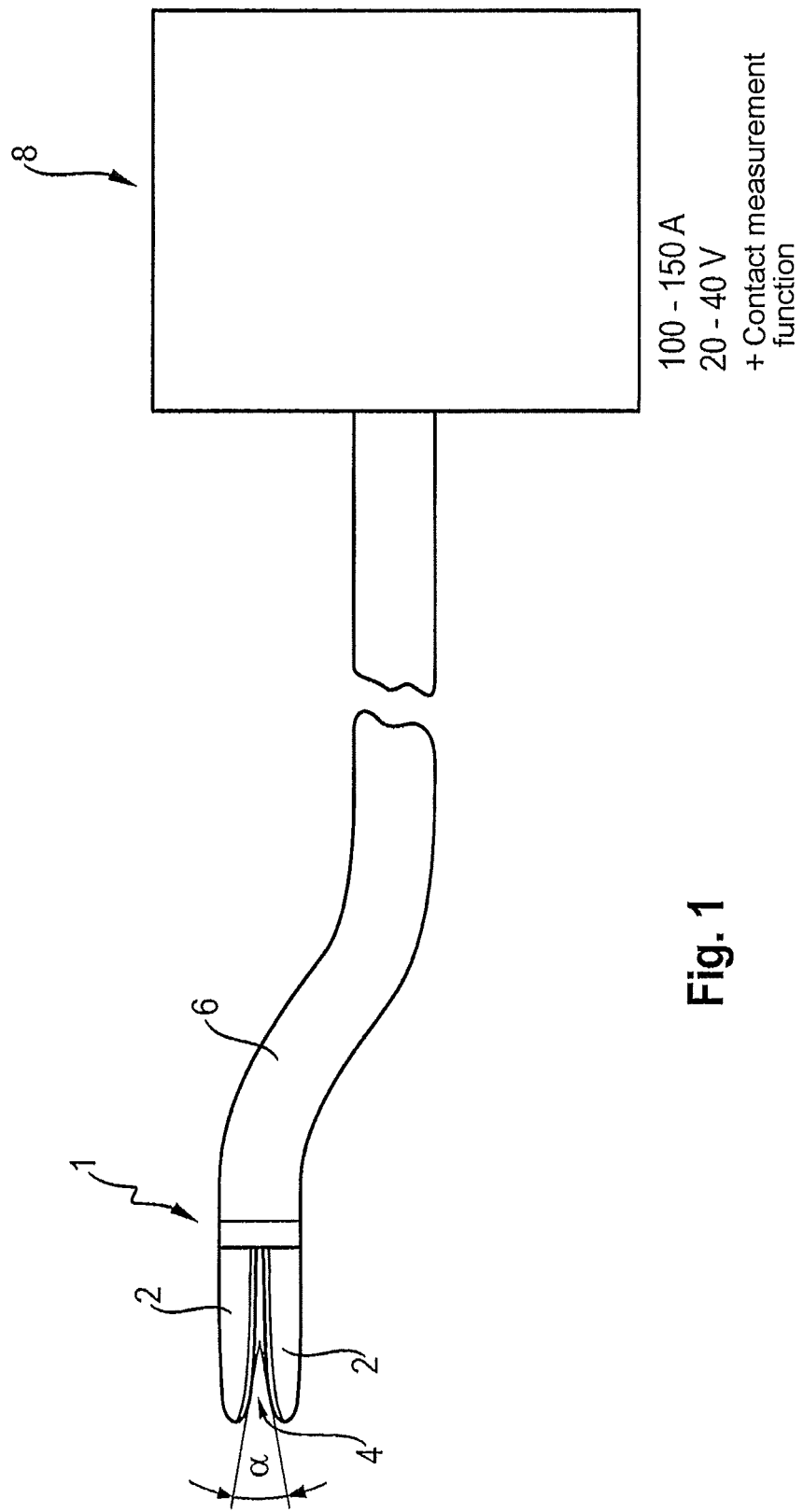

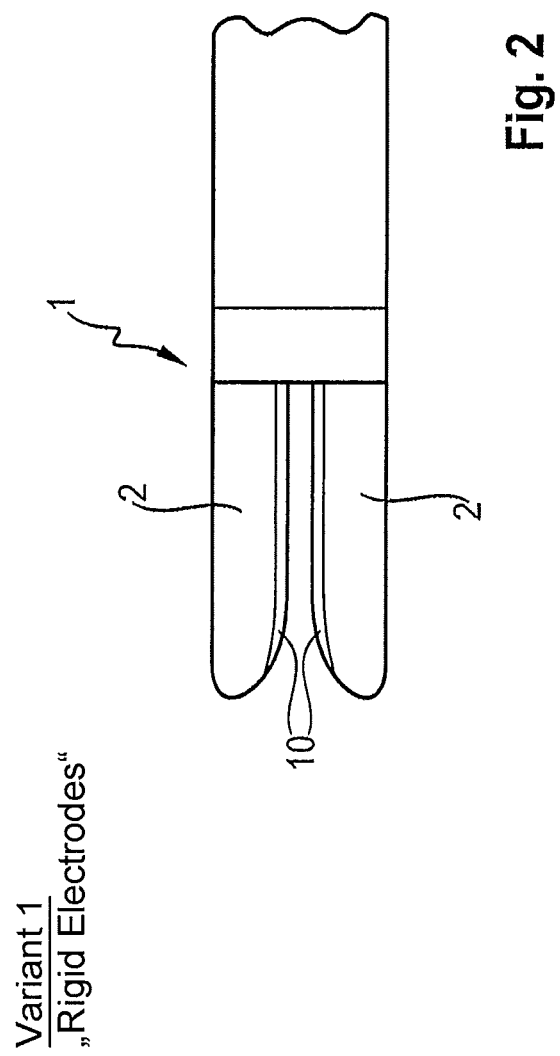

Variant 2
"Resilient Electrodes"

Variant 2

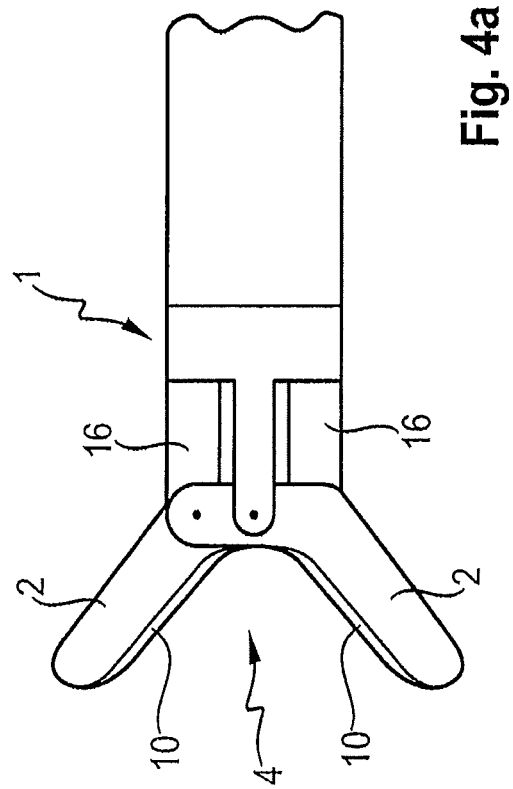

Variant 3

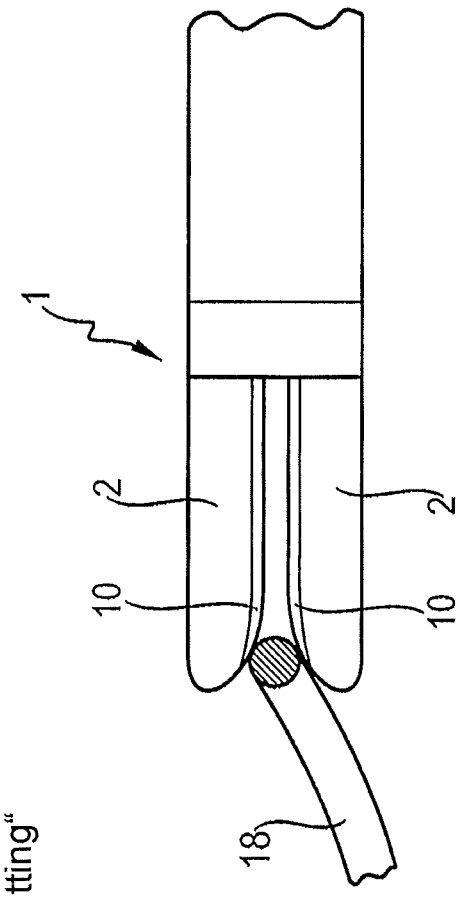

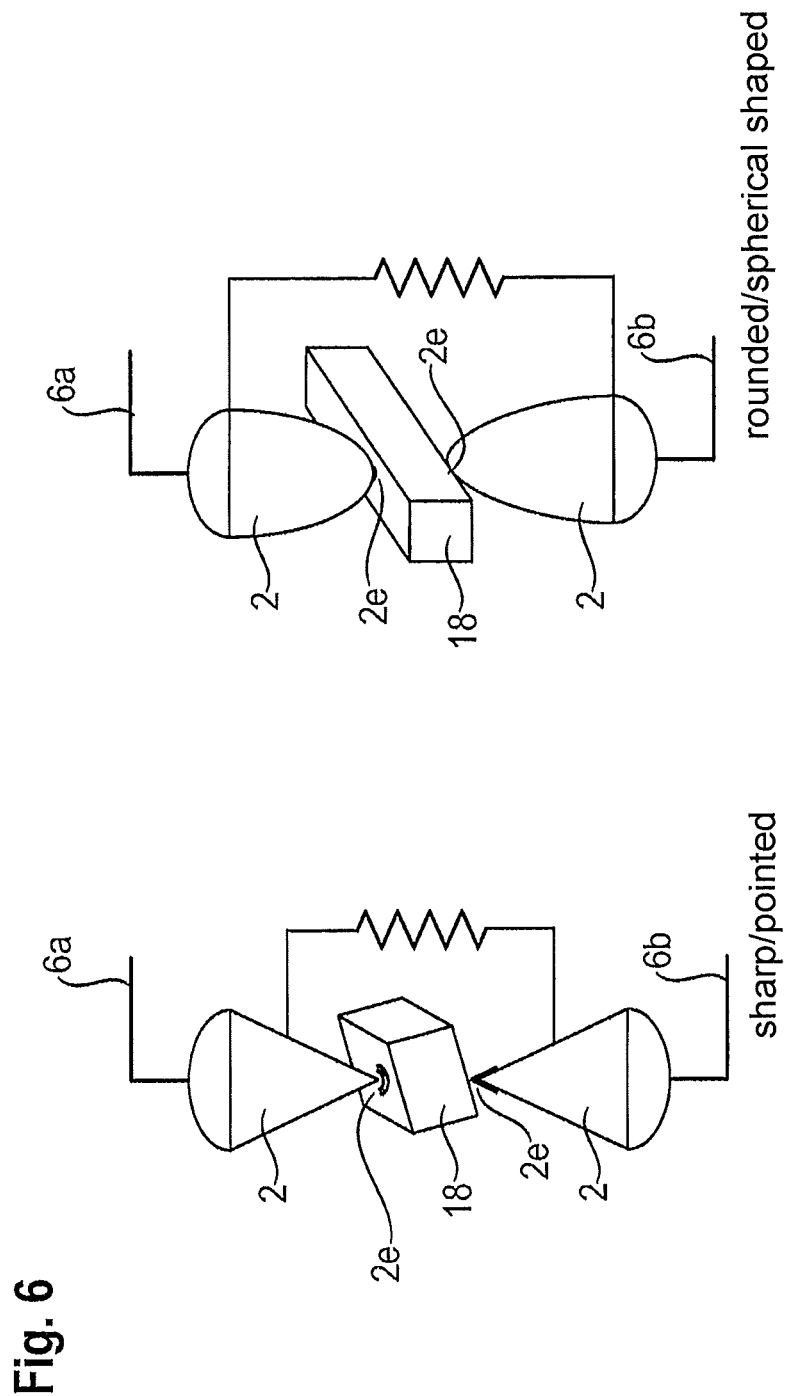

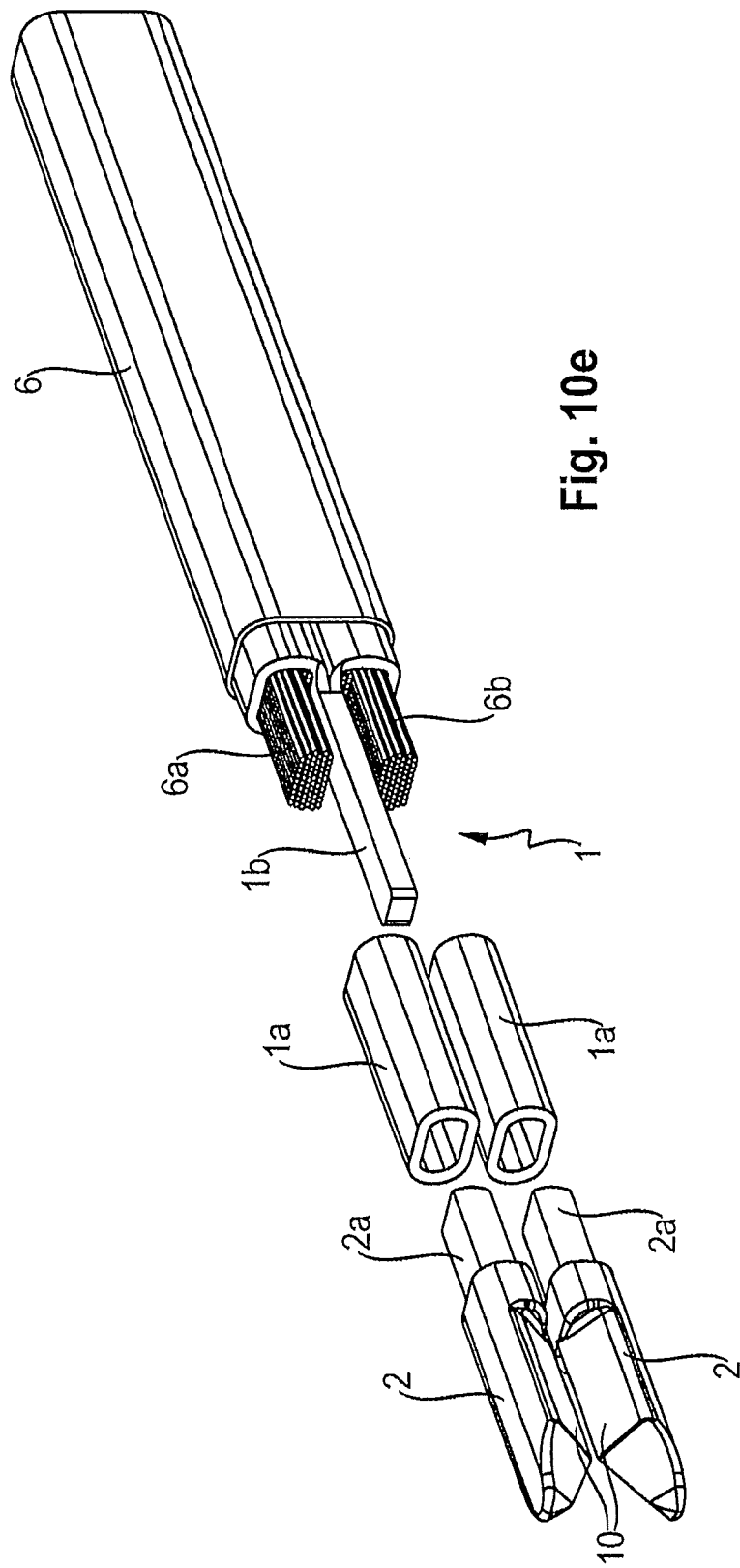

Fig. 14

| Material | Specific resistance in Ohms | Linear resistance-temperature coefficient in 1/K | Melting point | Specific heat capacity in kJ kg⁻¹ K⁻¹ | Specific weight in kg m⁻³ | Specific melting energy in J mm⁻³ (at 38°C) | Adjusted by resistance factor in $10^{15}$ J m⁻⁴ Ω⁻¹ |
|---|---|---|---|---|---|---|---|
| Silver | $1.59 \cdot 10^{-8}$ | 0.0038 | 961 | 0.235 | 10497 | 2.28 | 143 |
| Copper | $1.68 \cdot 10^{-8}$ | 0.0039 | 1064 | 0.382 | 8960 | 3.51 | 210 |
| Gold | $2.44 \cdot 10^{-8}$ | 0.0034 | 1084 | 0.130 | 19290 | 2.62 | 107 |
| Wolfram | $5.6 \cdot 10^{-8}$ | 0.0045 | 3422 | 0.134 | 19000 | 8.62 | 154 |
| Iron | $1.0 \cdot 10^{-7}$ | 0.005 | 1536 | 0.452 | 7500 | 5.08 | 50.8 |
| Unalloyed Steel | $1.43 \cdot 10^{-7}$ | | 1493 | 0.490 | 7800 | 5.56 | 39.0 |
| Titanium | $4.2 \cdot 10^{-7}$ | | 1668 | 0.522 | 4505 | 3.83 | 9.12 |
| Stainless Steel | $6.9 \cdot 10^{-7}$ | 0.0009 | 1147 | 0.477 | 7800 | 4.13 | 5.99 |
| Nickel-Titanium (Martensite) | $7.6 \cdot 10^{-7}$ | | 1310 | 0.45 | 6450 | 3.69 | 4.86 |
| Muscle Tissue | 2 | | | | | | |
| Drinking Water | 20 bis 2000 | | | 4.182 | | | |
| Distilled Water | 180000 | | | | | | |

SURGICAL CUTTER OPERATED WITH DIRECT CURRENT

The present invention relates to a surgical cutting device for fragmenting thin-walled and/or wire-shaped metallic implants, with direct current.

In the field of endoscopy so-called stents are often used for the therapy of e.g. constrictions, perforations and fistula, in particular in the alimentary canal of a patient. Such stents are tube-shaped networks which when compressed together or folded to minimum size are guided to a selected target location via an introduced endoscope or a trocar and then applied. After application the respective stent unfolds elastically to its complete size and can thus support the organ wall, or cover and close existing fistula or perforations.

Those stents which are provided to cover organ wall perforations often have a silicone membrane between their wire mesh. Thereby it is prevented that digestive juices and/or bacteria etc. get into the perforation or fistula and lead to an inflammation or at least hinder/prevent the healing process. After healing of the lesion such a stent can be recovered from the body, for which there is a plurality of recovery apparatuses in the state of the art.

However stents of this type can, in particular when they must remain for a long time in the body, grow into the organ tissue so that they must in part be torn out from the tissue with force, whereby naturally complications can occur, such as for example the creation of a new lesion and in the worst case a perforation.

Thereby implants which are to be subsequently removed concern not only grid-like stents according to the foregoing description but also tissue clips for the temporary anchoring of various measuring probes in a hollow organ or for the punctual closing of organ perforations, such as can occur for example in the removal of polyps in the alimentary canal of a patient. There also exist hook-shaped tissue anchors/expansion anchors whose tentacles drill into organ tissue and then can grow already after a short time.

In order to be able to explant implants of this type without danger for the patient, there exists the basic need for an instrument which makes the implant concerned more easily removable by cutting/cutting up of the implant material, and thus avoid possible complications. But since, as already indicated above, such implants consist mostly of metal or a metal alloy, which generally are designed to bear particular loads, mechanical cutting tools such as so-called endoscopic scissors, HF loops, APS, etc. are actually unusable, or at least unsuitable.

It has been shown, however, that only a surgical instrument for these particular purposes (explanting of metallic implants) can be used, that permits the implant material to be destroyed (fragmented) by partial melting, preferably segmentally. For this purpose HF instruments of the bipolar type have already been suggested, from which one is known for example from WO 2008/090003 A1.

The bipolar instrument disclosed therein serves the purpose of endoscopically controlled shortening and/or fragmentation of stents located in the gastrointestinal tract, in the tracheobronchial system or in other hollow organs, and has at its distal instrument head two instrument branches fixedly connected to each other, i.e. immobile relative to each other, which between them define a V-shaped tapering gap in the proximal direction. At an axial distance from the proximal end of the V-shaped gap is an electrode which is mounted to the instrument head or to the instrument branches, in an electrically insulating manner.

If now the instrument head is moved for example against a stent mesh, the mesh wire gets into to the V-shaped gap between the instrument branches, until it comes to lie at the end at the back of the gap. In this position the mesh wire then has an optimal distance to the electrode, whereby upon application of HF current an electric arc between the electrode and the mesh wire forms which makes the mesh wire melt.

Alternatively to the forming of an electric arc it has also been suggested in this prior art to bring the electrodes directly into physical contact with the stent material/wire and thus to directly introduce current into the stent wire for its heating. In place of the preferred HF alternating current it may according to this prior art also be provided to subject the electrode to a direct current or a low-frequency alternating current, for the forming of an electric arc.

The basic problem of this known instrument lies firstly in the forming of an appropriate electric arc between the welding electrode and the stent material. With different material thicknesses of the implant the distance to the electrode can change or be set differently, whereby the forming of the electric arc is influenced. Thereby the cutting capacity of the known instrument having rigid instrument branches cannot be stably maintained for all known implants.

Another fundamental problem is the heat input into the stent material. Namely, if electric current for example is introduced directly into the stent material, this heats up, which can lead to damage of the surrounding patient tissue. For this reason the said prior art also suggests a protective device which spaces the electrodes/stent wire from the patient tissue. Such a protection device increases the instrument cost and also makes it unwieldy.

In light of this problem it is an object of the present invention to provide a surgical implant cutter operating on the basis of direct current, which is introducible into the patient endoscopically or by means of a catheter, and whose cutting ability for different implants can be kept stable. A preferred aim of the present invention is also to make the surgical implant cutter as economical as possible without great design effort. Finally the surgical implant cutter according to the invention should preferably help to avoid application errors or at least indicate them.

This object as well as the preferred further objects are solved by means of an implant cutter having the features of claim 1. Advantageous configurations are subject-matter of the dependent claims.

The invention is thereby based on the following basic considerations:

In order to avoid tissue damage even in the absence of a special protection device, the heat input should be as small as possible and yet lead to a melting of the stent material. This may be achieved by keeping a contact surface/touching surface between electrode and stent material as small as possible (preferably punctiform or linear), in order to obtain a high current density in the contact region/transition (in the case of direct application of a direct current). I.e. the active contact surface/touching surface is configured at at least one electrode such that here the highest current density is achieved along the entire electrical current path. This is then sufficient to partially melt the stent material (only) at the contact point, without the entire stent being excessively heated.

Additionally or alternatively to this, the heat input should take place through direct application of an electric direct current, wherein the electric direct current is pulsed or cycled. Each resulting DC packet causes thermal energy input into the stent material, wherein the heat dissipation into the surrounding tissue is nevertheless small (in comparison to a non-cycled application of current) due to the inevitably short impulse duration.

The electrodes of the bipolar instrument should, additionally or alternatively to this, be arranged at the instrument tip such that the instrument itself deploys a sort of protective effect without having to arrange a special protection device according to prior art. For this purpose, the formation of two instrument branches extending in the longitudinal direction of the instrument, forming between themselves a (longitudinal) cutting gap, which instrument branches possess electrodes or form electrodes at their respectively facing sides, has been shown to be advantageous. Therefore the electrodes inevitably turn away from the surrounding tissue, wherein the branches arrange themselves shieldingly between the electrodes and the surrounding tissue.

To limit to a minimum the effective energy input into the stent material it is advantageous to know or to determine it. Therefore, additionally or alternatively to the above mentioned measures, a measuring device may be provided which preferably determines the electrical resistance at the transition region/contact region between electrode and stent material, and from this the electric current value that is sufficient for a partial melting of the stent material is set.

Additionally or alternatively to this the electrode material also has a predetermined material property which counteracts or prevents/restricts a thermal wearing of the material. For this purpose, the term "resistance-adjusted specific melting energy" as the predetermined material property is introduced at this point into this application. This is calculated essentially from material-specific constants such as the specific heat capacity c, the mass density p, the melting temperature $T_S$ and the specific electrical resistance r. This material property allows a direct comparison of various materials to the effect of how fast these materials are melted by a given electric current flow (the lower the resistance-adjusted specific melting energy, the faster a material is melted by the given current flow). The value of the resistance-adjusted specific melting energy for the electrode material should, according to the invention, be higher than that of the stent material, preferably by at least a factor of two.

An aspect of the present invention consists now in that, in the case that the mutually opposing instrument branches forming a cutting gap are each equipped with an electrode, or each forms an electrode, the implant material to be fragmented obtains direct electrical and physical contact with the electrodes (in other words shorts these) in the event of its introduction into the cutting gap, whereby a direct current (short circuit current) is conducted through the implant material (without arcing), which leads to its partial heating. In other words the implant material located between the electrodes is strongly heated upon suitable choice of current strengths, and begins to partially melt (between the electrodes) and to flow/drip. If thereby the instrument head optionally moves further into the implant material, the two instrument branches effect optionally additionally a dissecting of the melted implant material with low mechanical feed force, which may be applied problem-free for example via the instrument shank within the insertion tool (endoscope, trocar, etc.).

In the case of this arrangement the forming of an electric arc as well as the design effort for setting up a correct distance between the implant material and an electrode, according to the known state of the art, is not required, whereby the instrument can be made substantially more easily and thereby more economically. In addition the subject-matter of the present invention differs also fundamentally from known TFT-instruments of the bipolar type (tissue fusion instruments) whereby indeed also two instrument branches with electrodes are equipped for tissue dissecting or tissue welding (coagulation), but on the one hand HF-current is applied to the electrodes, and on the other hand the instrument branches must be movable with respect to each other in order to clamp between these the patient tissue to be treated, with a predetermined contact pressure. In contrast to this however the metallic implant material according to the invention is melted by the DC short circuit at least to the extent that it can be easily dissected by the instrument branches by sliding the instrument head forwards.

Furthermore it is a requirement to be fulfilled by the dimensioning and design of the electrodes that, in the decisive contact closure between the electrodes or between at least one of the electrodes and the implant, a particularly high current density is formed because of a locally reduced current path resulting there. That means the contact area and therefore the current path between the at least one electrode and the implant must be so small that the high current density arising there leads to a melting of the implant material (only) between the electrodes. This is achieved by the at least one electrode (or the electrodes at both branches) having a region provided for the contact engagement with the implant, which shows or defines an (essentially one-dimensional) contact line preferably in the longitudinal direction of the electrodes, or an (essentially one-dimensional) contact point, oriented to a plane (i.e. by contact of the electrode on a flat surface). Such a contact line results, for example, when the respective electrode is provided with a cutting edge or forms said cutting edge. It is also conceivable that the at least one electrode at its side facing the other electrode is outwardly longitudinally curved, either convexly or shaped as a channel. If such a channel is placed at its outer periphery on one plane, there arises unequivocally an (essentially one-dimensional) line contact or even point contact. The possibility also exists to form the at least one electrode with a narrow longitudinal ridge which forms a (sharp-edged) contact strip on the electrode which protrudes to the other electrode. Finally it is also conceivable to make the at least one electrode spherical cap-shaped in order to realize/approximate an essentially point contact.

In order not to damage the surrounding patient tissue, it would be advantageous if DC current impulses of high current strengths (of up to 200 amperes, preferably between 100-150 A), are applied in fractions of a second and by means of control technology, to the mutually opposing electrodes between which the weld gap is formed in the longitudinal direction of the instrument. The metal is thereby melted and cut between the electrodes without the implant material in the vicinity of the cutting gap heating up excessively. The reason for this, as already indicated above, is that by means of current pulsing, the heat dissipation effect from the stent into the surrounding tissue can be reduced. The voltage may thereby lie far below a limit of 48 Volts for a low voltage (preferably between 20-40 V), which is completely harmless for the patient.

Naturally the possibility exists to make/position the two instrument branches and/or the electrodes assembled on them elastically resiliently, so that even implants with larger material thicknesses can be inserted into the weld gap and rest securely at the electrodes. Thereby it may even be provided to move the branches via an actuating mechanism in order to adjust to the weld gap (gap width).

In order to be able to melt and dissect the implant material sufficiently safely—also for the patient—it would be advantageous when the branches and/or electrodes at their respectively facing long sides are shaped to form a narrow cutting edge or knob as sole effective contact area, to achieve almost a one-dimensional line contact or nearly point contact with the implant material. The implant material heats up at this contact location having very small surface, particularly due to the high current density, and can be thereby quickly melted before the implant material located further away heats up. For this purpose it has shown to be particularly advantageous when at least the electrodes are made from a heat resistant material such as wolfram or from a low-alloy steel.

In order to optimize the dissecting process, the two electrodes and/or the two instrument branches may be oriented with respect to each other to be essentially V-shaped, so that the welding gap/cutting gap forming therebetween narrows in the proximal direction, continuously linearly or in a convex curve shape.

Also a sort of biasing device may be provided at the instrument tip, which biases the electrodes and/or the instrument branches against each other with a predetermined biasing force so that an implant material introduced therebetween becomes almost automatically compressed/crushed on both sides.

It can be taken from the foregoing description that the gripping quality or contact quality between implant material and electrode plays a large role in ensuring a safe dissecting of a metallic implant material. More specifically, the smaller the contact surfaces between implant and electrodes, the faster the implant material melts in the contact region between the electrodes, and the smaller the energy input into the stent material can be. Therefore according to the invention an electric/electronic detection of contact quality (measuring device) is optionally provided which, in the event of an actuation of the instrument and (chronologically) before the resulting application of the DC power current/cutting current to the electrodes, performs a test sequence (automatically always, or selectively). In this case the contact resistance between the respective electrodes and the implant material is determined upon applying to the electrodes for example a very small test current distinctly below the welding/cutting current, or with the power current but for an extremely short impulse time, so that the implant tissue does not heat up, or only negligibly heats up, and in the case that the resistance falls below a threshold (contact resistance is too low) the user is warned and/or the subsequent DC power current application (cutting current application) blocked. Additionally or alternatively the amount of the DC power current to be delivered may be adjusted based on the result of the determination so that a melting of the implant material is ensured.

Furthermore it may also be checked in the test sequence whether the required DC power current would exceed the load capacity of the supply lines and/or of the cutting electrodes, in order to avoid damage or a rapid wear of the cutting instrument.

Generally stent implants are made from stainless steel or a titanium alloy (martensite). Experiments according to the invention revealed for the generally known common stent materials a resistance-adjusted specific melting energy of between 4.86 and 5.99 $10^{15}$ J m$^{-4}$ $\Omega^{-1}$. Consequently a further aspect of the invention, optionally to be claimed independently, provides a resistance-adjusted specific melting energy for the electrode material larger than 5.99 $10^{15}$ J m$^{-4}$ $\Omega^{-1}$ preferably by a minimum of a factor of 2. In this way a fast thermal wearing of the electrode material is counteracted.

The invention will be explained in more detail below with reference to preferred embodiment examples with reference to the accompanying drawings.

FIG. 1 shows the conceptual arrangement of a surgical implant-cutting instrument operated with direct current and of the bipolar type, according to a preferred exemplary embodiment of the present invention, FIG. 2 shows the conceptual construction of two rigid instrument branches at a distal instrument head, FIGS. 3a and 3b show the conceptual construction of two elastic or elastically supported instrument branches at the distal instrument head in operating positions extended from and retracted into an insertion tool, FIGS. 4a and 4b show the conceptual construction of two simply supported instrument branches at the distal instrument head, with widened and narrowed cutting gap, FIG. 5 shows the conceptual construction of two instrument branches at the distal instrument head in contact engagement (short circuit engagement) with an electrically conductive implant, FIG. 6 shows the gripping or contact engagement principle between the cutting tool according to the invention and the electrically conductive implant, FIG. 7 shows a comparison chart between the resistance-adjusted specific melting energy and the respective current density along an instrument-implant-current path, FIG. 8 shows a resistance circuit diagram of the instrument-implant-current path for a test sequence of an electric/electronic contact quality detection device of the instrument control.

FIGS. 10a to 10e show a preferred exemplary embodiment for the construction of the instrument tip and/or of the instrument branches/electrodes.

FIG. 13 shows the electrical current path according to FIG. 11 as well as the thermal effect on an implant in the transition region/contact region between implant and electrodes and FIG. 14 shows a table referring to the energy absorption characteristics of different electrically conductive materials.

Figure 3A:
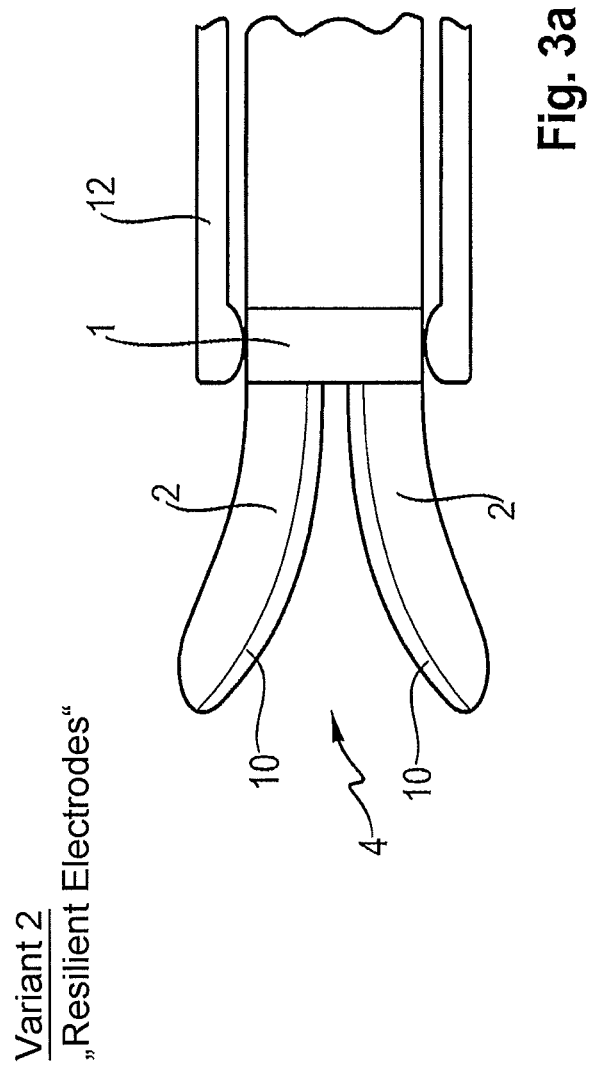

The surgical implant-cutting tool of the bipolar type shown schematically in FIG. 1 has a distal instrument head or an instrument tip 1 with (at least) two instrument branches 2 which therebetween define a longitudinal gap 4 extending in the longitudinal direction of the instrument. The instrument head 1 is mounted at a distal end of a preferably bendably flexible (or alternatively rigid) instrument shank 6 having at least two poles and which in turn is attached to a controlled/guided or controllable/guidable DC current generator 8. The DC current generator 8 delivers a direct current of preferably optionally between 100 A-150 A with a voltage of preferably optionally 20 V-40 V.

As can furthermore be seen from FIG. 1, the gap formed between the instrument branches 2 has essentially a V-shape that narrows in the proximal direction. The instrument shank 6 and also the instrument head 1 have an outer diameter (for example 6 mm max.) that permits the surgical instrument to be insertable into the (standardized) working channel of an endoscope, trocar or similar insertion tool, which is known per se. Alternatively the instrument shank and instrument head may be configured and dimensioned such that it can be introduced in the manner of a catheter (without insertion tool) into a patient's hollow organ.

FIG. 2 shows in enlarged view a variant for a branch construction according to the invention.

Therefore the instrument branches 2 are connected to the instrument head 1 and in addition executed to be rigid. Electrically conductive electrodes 10 are arranged on the mutually facing longitudinal sides of each branch 2, which electrodes 10 are connected via two electrical conductors (not shown) inside of the instrument shank 6 with the DC current generator 8. The branches 2 may thereby themselves form the electrodes 10, for which they must however be electrically insulatedly fixed to the instrument head 1. Alternatively the instrument branches 2 may however even be equipped/loaded with external electrodes 10. The formation/arrangement of the electrodes 10 as well as of their connection to the DC current generator is the same for all the variants that are described in the following, so that it is not described repeatedly.

Figure 3B:
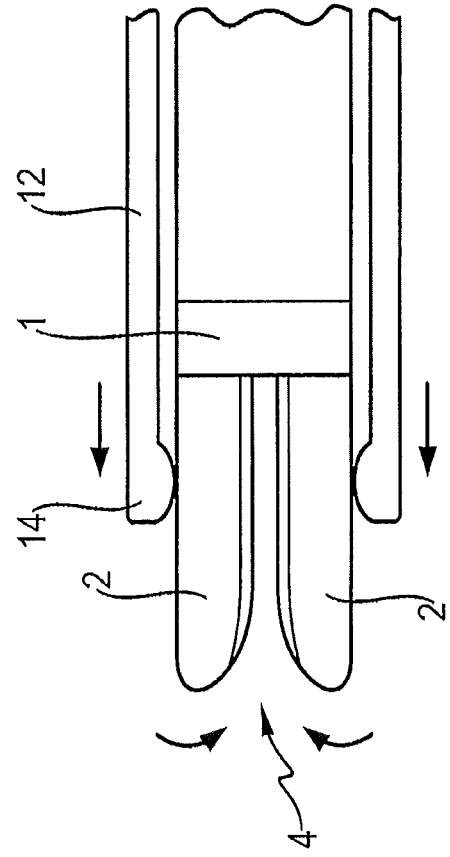

According to the variant shown in FIG. 3 the branches 2 and/or the electrodes 10 are made from a bendably flexible, preferably elastic material, or the electrodes 10 are spring-loaded against the respective instrument branches 2 such that they can be elastically pushed into the branches 2 under increasing gap width.

According to FIG. 3 an outer sleeve 12 is provided at least at the distal end region of the instrument, which is axially movable relative to the instrument. This sleeve 12 may be a separate component or the insertion tool itself. Thereby the instrument is shown in a position in which the instrument head 1, or at least the instrument branches 2, extend axially from the sleeve 12 and in addition spread apart radially (elastically), whereby the cutting gap 4 widens.

Figure 4B:
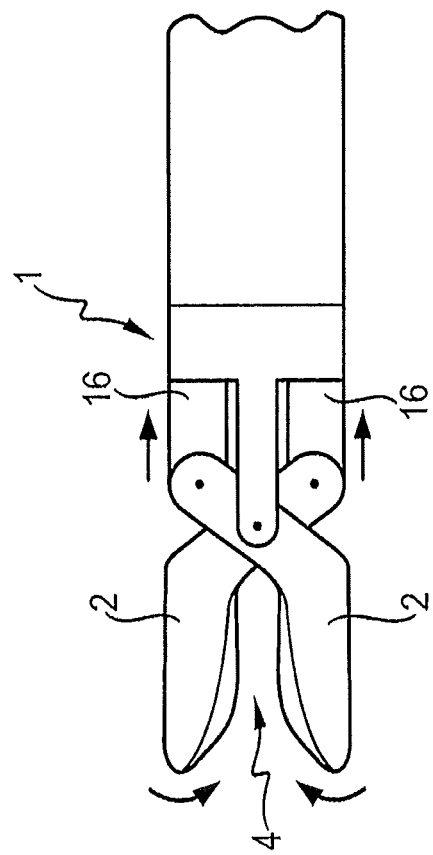

According to FIG. 4 the instrument head 1 or the instrument branches 2 is/are withdrawn into the sleeve 12, or the sleeve is advanced, whereby the instrument branches 2 are compressed together against their own elasticity when the cutting gap 4 narrows. To specify this compression process more precisely, the sleeve 12 may be shaped at its distal end to form an inner ring or torus 14 which enters into/remains in sliding engagement with the instrument head 1 or the instrument branches 2, with guiding quality.

A third variant of a branch construction is shown in FIG. 5. In this case the branches 2 per se are preferably rigidly formed, while also being pivotably supported (like scissors) at the instrument head 1. Furthermore an actuation device or setting device in the form of a pullrod/pushrod 16 is provided, which is hinged at the branches 2 to transform an axial movement of the rod 16 into a pivoting movement of the branches 2. In this way the cutting gap between the branches 2 can be adjusted.

According to FIG. 5 the branches 2 are shown in a maximum gap width position, whereas FIG. 6 shows the instrument with instrument branches 2 closed together by means of the setting device, to define a minimum gap width.

Figure 7:
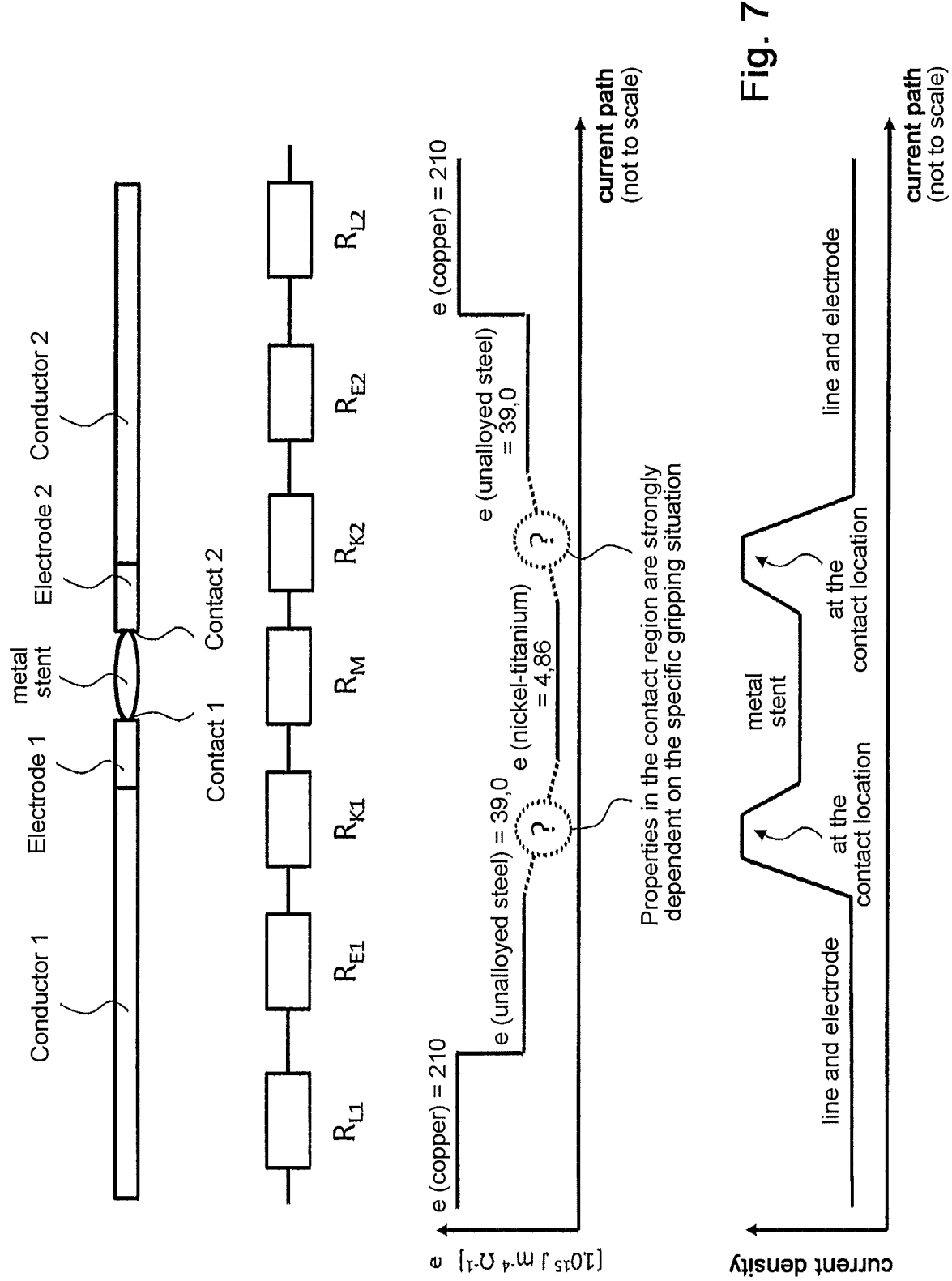

In FIG. 7 the functional principle of the DC powered implant-cutting instrument of bipolar type, according to the invention, is shown.

Accordingly the instrument branches 2 are basically spaced or spaceable such that the cutting gap 4 which forms longitudinally therebetween has a gap width which permits/ensures an introduction of an implant or implant section 18 (stent wire) into the gap 4 when coming into contact with the two mutually opposing longitudinal branches 2/electrodes 10. Preferably the instrument branches 2 are for this purpose banana-shaped/convexly rounded at least in the region of their distal (free) end sections, to form a convex longitudinal curve, at least in longitudinal sections, at the mutually facing branch sides. In this way the cutting gap 4 tapers not (necessarily) linearly, but rather along a curve. It goes without saying that the electrodes 10 are suited to fit this curve path.

If now a metallic implant or an implant section 18 is introduced into the gap 4, generally the implant material already at the distal end portion of the instrument branches 2 comes into contact with the respective electrodes 10 and shorts them, whereby because of the applied power current the implant material between the electrodes 10 is heated and melted.

If now the instrument head 1 moves forwards, the implant 18 slides deeper and deeper into the tapering cutting gap 4, wherein the electrodes 10 preferably also dissect the melted implant material.

The following parameters are, among others, of importance for the described cutting process:
- The electrodes 10 or the instrument branches 2 should preferably have a form which favors the dissecting process.
- The contact resistance between the electrodes 10 and the implant 18 should be as high as possible in order to securely melt the implant material in the contact region (i.e. from the outside inwards), but additionally to leave implant regions further away to be unheated as much as possible.
- The energy input into the implant material should take place such that a heat dissipation into the surrounding patient tissue remains as small as possible, even in the absence of additional protection measures.

For this reason the instrument branches 2 and/or at least the electrodes 10, according to a preferred exemplary embodiment of the invention, comprise a sort of blade shape with a narrow (sharp) longitudinal edge on the mutually facing longitudinal sides of each branch 2. By means of this form an (essentially one-dimensional) line-like or point-like contact with the implant is achieved, whereby at this position the contact resistance and with it the current density and the material heating created in this way becomes particularly high with application of DC current. A preferred construction for an instrument branch 2 and/or electrode, according to the invention, is shown in FIG. 10a ff.

Figure 10A:
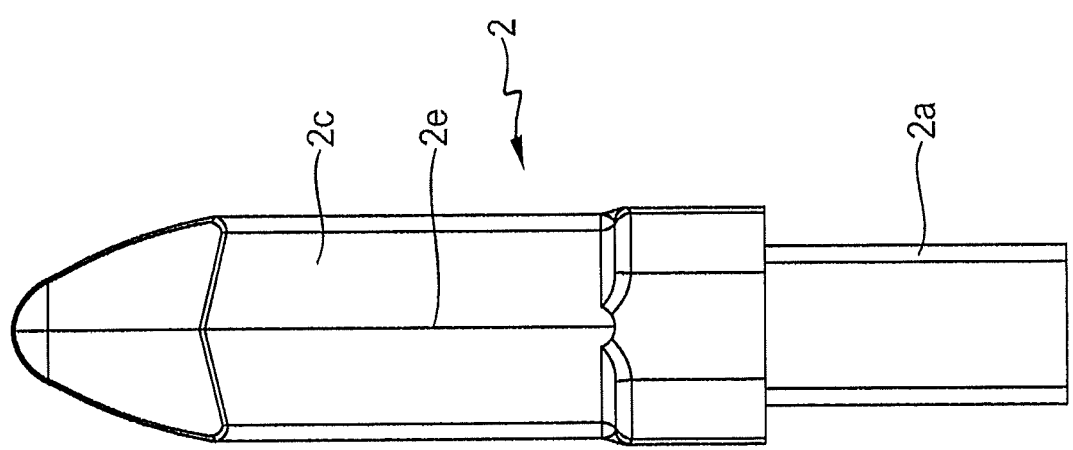
Figure 10B:
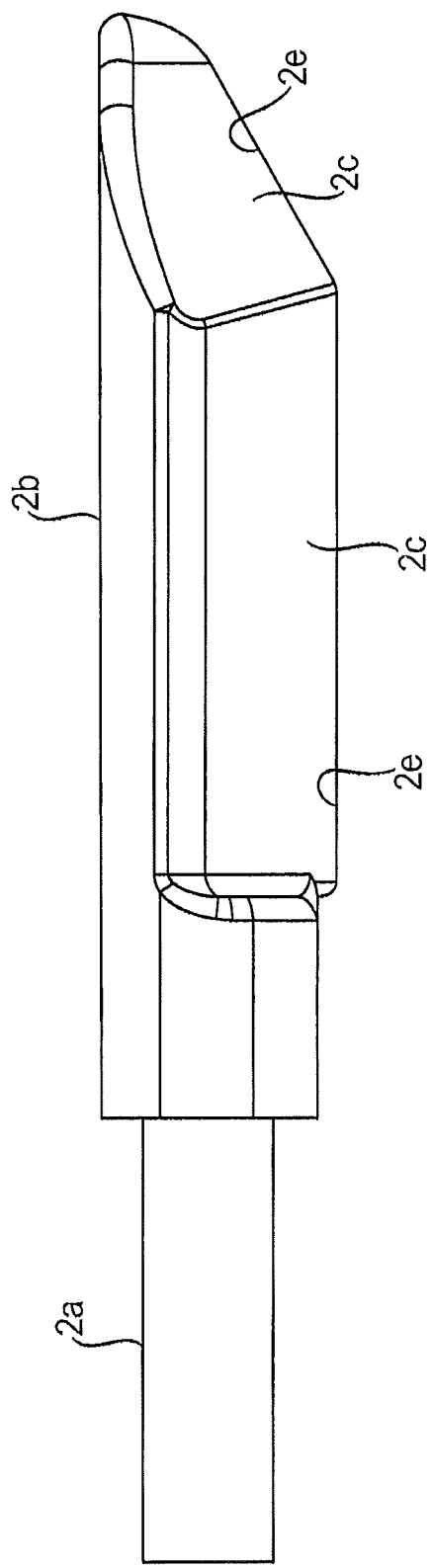
Figure 10C:
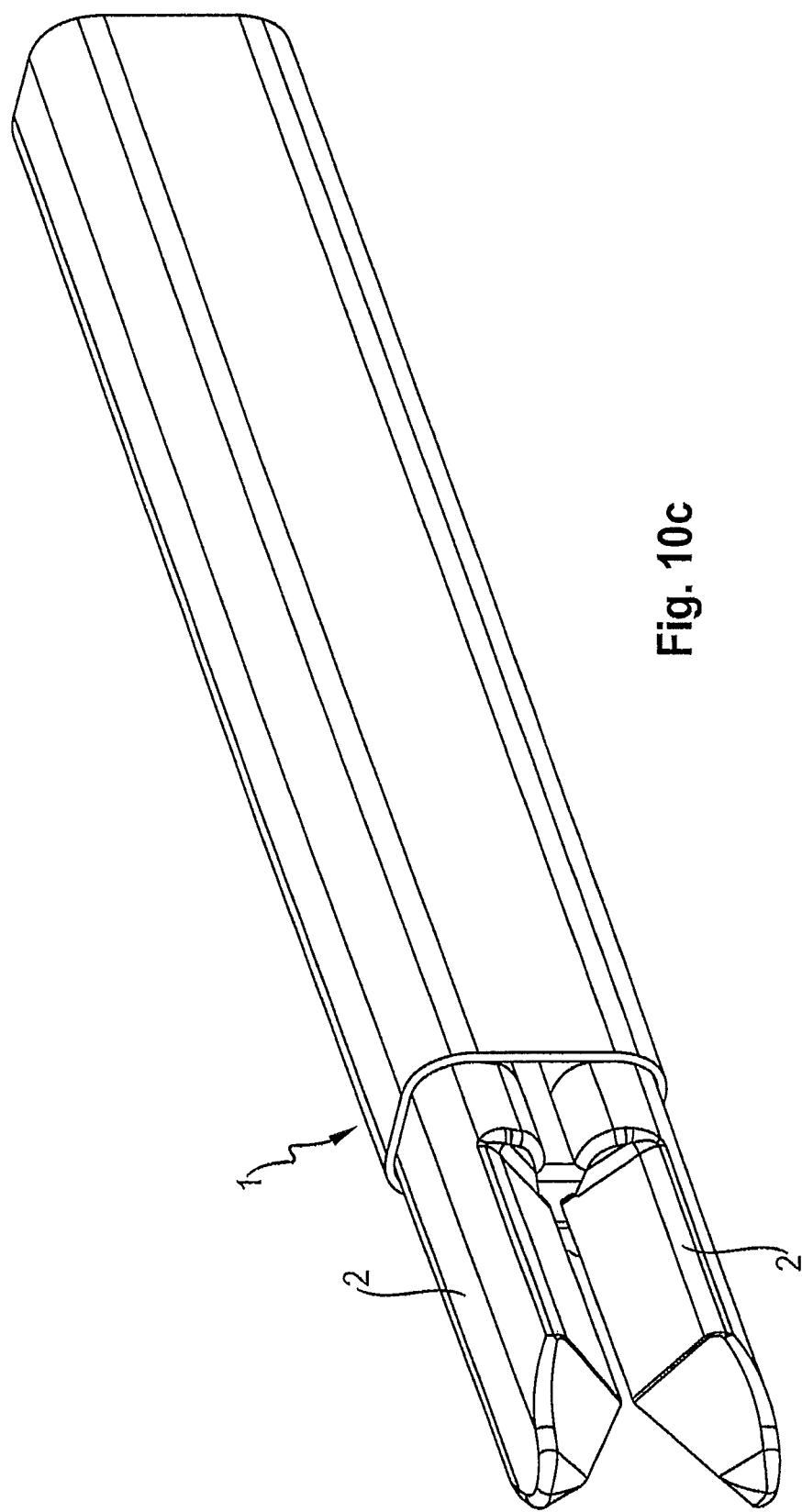
Figure 10D:
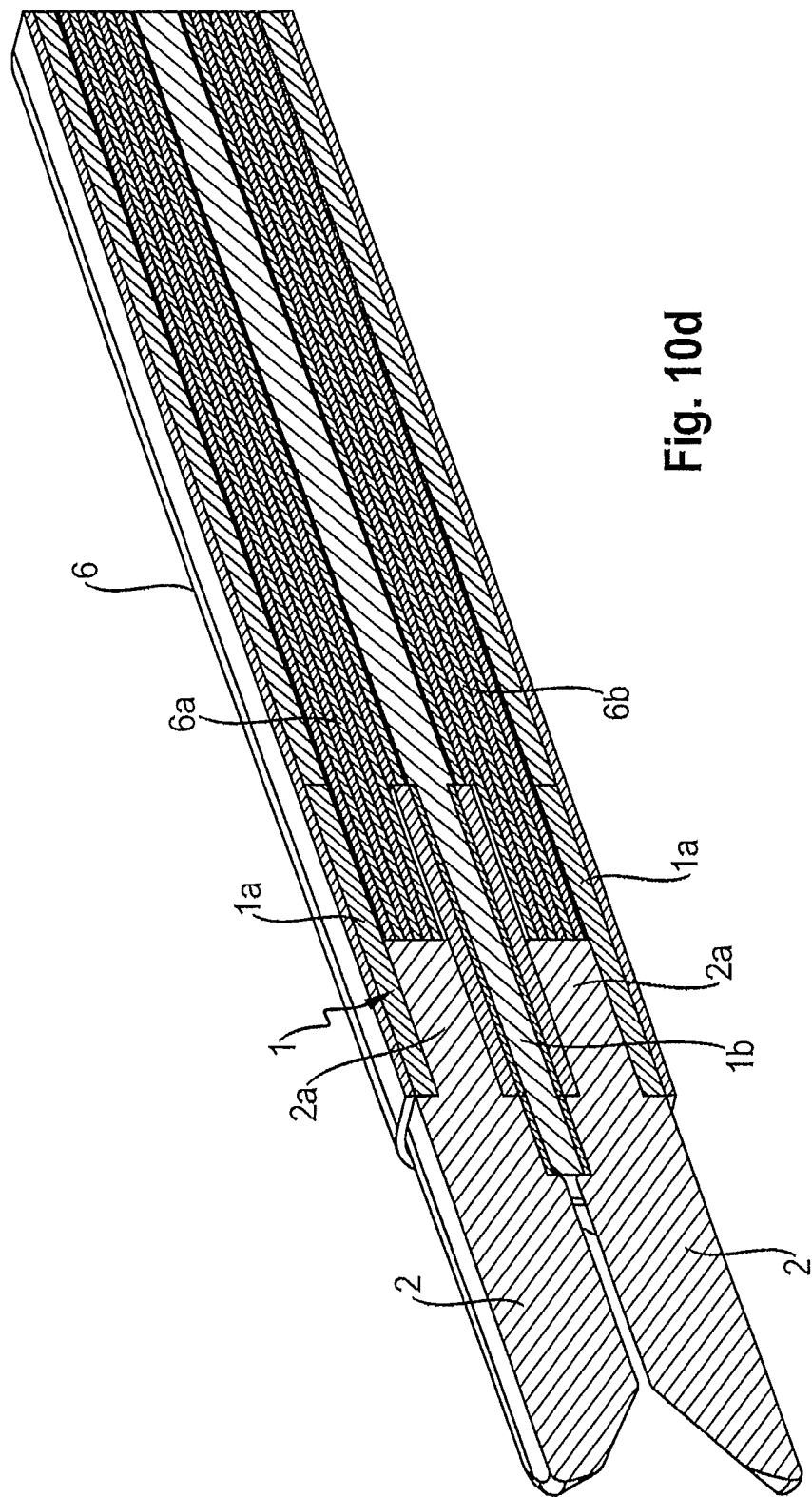

According to FIGS. 10a and 10b the instrument branch 2 and the electrode 10 in the preferred exemplary embodiment are formed (materially) integrally, i.e. the instrument branch 2 forms at the same time the electrode 10. Accordingly the instrument branch 2 is made from a heat resistant material, preferably wolfram or a low-alloy steel.

Each branch 2 is shaped at its proximal end section into a sort of hollow pin 2a which is inserted in a corresponding receiving socket/receiving sleeve 1a on sides of the instrument head 1, in accordance with FIG. 10e. Accordingly two receiving sleeves 1a are provided for the two branches 2, which according to FIG. 10e are separated from each other by an insulating piece/distance piece 1b of the instrument head 1.

The distal section of each branch 2 is formed (ground/milled) into a blade shape having a partially circular-shaped back of the blade 2b and a blade edge 2c which is curved to be banana shaped in the longitudinal direction. Alternatively the blade shape may be configured such that two (straight) longitudinal sections are provided standing obtusely with respect to each other, whereby the banana shape is approximated with the forming of a single kink. In this way a narrow (sharp) longitudinal edge/cutting edge 2e occurs at the one longitudinal side of each branch 2, which extends arcuately in the longitudinal branch direction (corresponding to the longitudinal direction of the instrument).

Two conductor bundles 6a, 6b consisting in each case of a plurality of individual litz wires project from the instrument shank 6 at its distal end, wherein the conductor bundles 6a, 6b are both inserted in the receiving sleeves 1a and crimped. In this way each instrument branch 2 or electrode 10 comes into electrical contact with a respective conductor bundle 6a, 6b, which in turn are connected to the DC current generator.

By means of the foregoing instrument design the conductor bundles 6a, 6b can achieve a comparatively large conductor thickness despite a low maximum shank outer diameter in order to conduct a sufficient electric current with comparatively lower current density (without it heating up). The passage from each conductor bundle 6a, 6b is made preferably from copper on the associated branch 2, preferably from wolfram/steel over the clamping sleeve 1a and thereby without large losses. Each branch 2 thereby forms a cutting edge 2e, which also simultaneously defines the contact line with the implant 18 and which thus generates a high contact resistance (and with it a high current density). At the same time the cutting edge 2e serves preferably for the mechanical dissecting of the electrically melted implant material.

In order to ensure the correct contact closure with the implant 18, the surgical instrument has a contact-quality-detection function, as will be described in the following with reference to FIGS. 6-9.

The contact grip between instrument and implant is functionally depicted in FIG. 6. Ideally an electric current is guided via the copper conductors 6a, 6b in the instrument shank 6 to the instrument branches 2 and from there introduced via the point or line contact into the implant section between the branches. As accomplished in the foregoing, a high contact resistance is thereby achieved.

But now the situation can arise that the implant 18 is not clamped exactly between the contact edges 2e of the instrument branches 2 or electrodes, but rather bears over a large area on the electrode of each branch 2. In this way the contact resistance between the electrode and the implant would be distinctly reduced (current density reduces) such that much more current would have to be conducted in the conductors 6a, 6b in order to achieve a melting of the implant material. This serves to avoid heating of the entire implant.

FIG. 7 shows the course of the material properties in the current path of the surgical implant-cutting instrument.

To understand the material choice/material properties according to the invention, the term "resistance-adjusted specific melting energy" e is to be introduced, as is given in FIG. 14 for some selected materials. This measure describes how easily a specific volume (e.g. 1 mm³) of a conducting material (e.g. a predefined metal) can be melted by a current flow. This measure is calculated according to the following formula:

$$e = c \cdot V \cdot \rho \cdot (T_S - T_0) \cdot \frac{1}{r}$$

having the following parameters:
e resistance-adjusted specific melting energy
c specific heat capacity
V material volume
ρ mass density
$T_S$ melting temperature
$T_O$ temperature before energy input
r specific electrical resistance The situation according to FIG. 14 is shown exemplarily for the following materials:
Conductor: copper
Electrode: unalloyed steel
Metal stent: nickel-titanium The resistance-adjusted specific melting energy e for each of these metals is approximately (given in $10^{15}$ J m$^{-4}$ Ω$^{-1}$):
Copper: 210
Unalloyed steel: 39
Nickel-titanium: 4.86

This means that with identical current flow having identical current density, nickel-titanium melts faster than unalloyed steel by the ratio 39 to 4.86 (approx. 8×), while nickel-titanium melts faster than copper by the corresponding ratio 210 to 4.86 (approx. 43×). This assumes the same current density in the material. Moreover this means that it is made possible, through material choice on the basis of the resistance-adjusted specific melting energy, to dose an electrical direct current which flows through the conductor, the electrode and the stent material, such that it selectively melts the stent material while the electrodes and the conductor do not reach the melting temperature during the current impulse. Preferably the materials are selected such that the resistance-adjusted specific melting energy of the materials which are not to be melted (in particular conductor material and electrode material) is at least twice the resistance-adjusted specific melting energy of those materials that are to be melted (in particular the material of the implant to be cut).

Furthermore, and on this basis, it is provided according to the invention to control the current density such that the current density in the target metal to be melted is higher than in the conducting lines and electrodes of the instrument. This is solved by the configuration, according to the invention, of the electrodes whereby a punctiform or linear contact surface is created between electrode and the metal to be cut, which leads to a high current density. In this way the melting of the target material is additionally accelerated in comparison with the electrode material and conductor material. The contact quality between electrode and the metal to be melted is strongly dependent on each gripping situation. An optimal contact quality is promoted by the configuration, according to the invention, of the electrodes. In addition, according to the present invention it is useful to carry out an electrical check of the contact quality.

The resistance path along the electrical path is marked out in FIG. 7. As can be clearly seen from this, the two contact locations represent resistance peaks, while the current is guided nearly without losses in the remaining path sections. Now in order to determine the contact quality, the invention provides the execution of a test sequence which is performed with each new operation, automatically or optionally on manual command, and which is shown schematically in FIG. 8.

Consequently the individual conductor sections of the electrical path form individually identifiable resistances from which only the contact resistances $R_{K1,2}$ are initially of interest. The conducting path is thereby formed from the conductor bundles 6a, 6b in the instrument shank 6, the branches 2, the contact locations as well as the implant 18. In order to determine the contact resistances exclusively, for example a small test current below the later cutting current is applied to the electrical path and a reference voltage is directly tapped at the distal end of the conductor bundles 6a, 6b. The conductor bundle resistance may be calculated from the difference between the applied voltage and the tapped voltage. Furthermore the contact resistance $R_{K1,2}$ can be determined in this way. According to the amount of the contact resistance $R_{K1,2}$, the contact-quality-detection function has the ability to give a warning signal for an incorrect gripping position and/or to block the supply of a cutting current and/or to correct the amount of the cutting current to below the load limit of the conductor bundles 6a, 6b.

It should be noted at this point that in place of the small test current, alternatively the cutting current or power current itself may be used for test purposes, wherein in this case the cutting current may be applied for only a short time in order to keep the energy input into the implant smaller than the energy input that would be required to melt the implant material.

Figure 8:
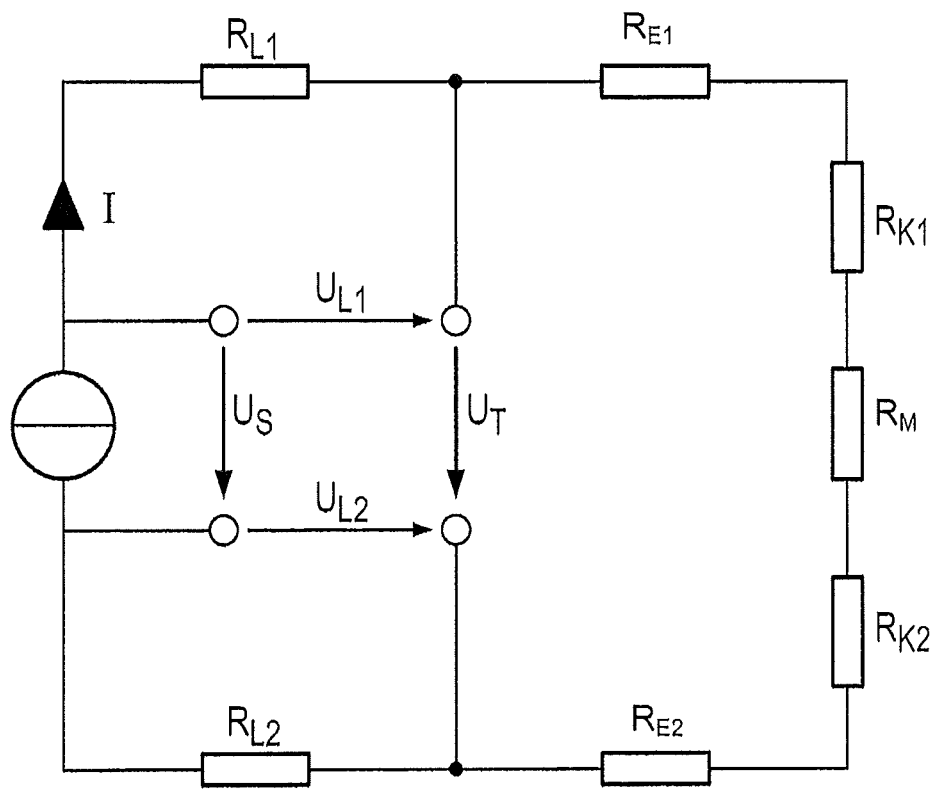
Figure 9:
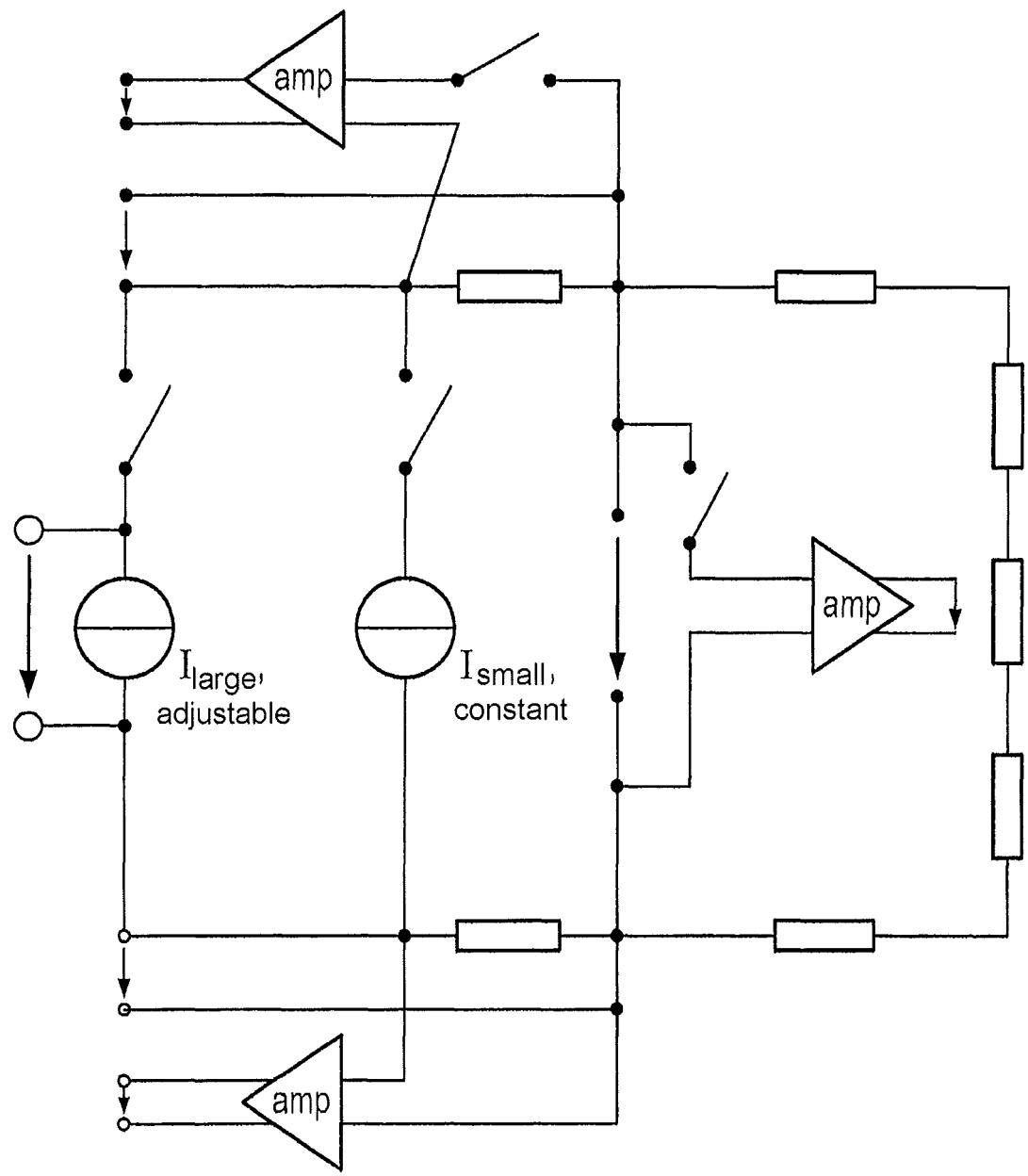
FIG. 9 shows a resistance circuit diagram of the instrument-implant-current path for an application of power current (cutting sequence) of the instrument control.

For the subsequent cutting according to FIG. 9 a circuit (see FIG. 9) suited for the implementation of the functional principle according to FIG. 8 is actuated in order to disable the initially applied test current/power current sequence, and to replace it with a power current (cutting current) which, as is shown, is controllable at least dependently on the predetermined contact resistance $R_{K1,2}$. Furthermore, factors such as the cutting temperature, the voltage level, the temperature in the conductor bundle, etc. can influence the setting procedure of the cutting current. Optionally an "emergency stop" function may be provided, which for example in the case of a contact break at the electrodes switches off the current supply in order to avoid arcing.

Operation of "Metal Separation with DC Current" According to the Present Invention
Basic Energy Consideration The crystal lattice of a metal has a characterizing thermal energy which manifests itself in vibrations of the atoms of the lattice. Thermal energy is thereby a kinetic energy.

The thermal energy of a material is dependent on the temperature T, the mass m and a material constant c (specific heat capacity), and can be expressed with the following formula:

$$E_{th} = c \cdot m \cdot T$$

An electric direct current which flows through a metal lattice leads to an excitement of the lattice atoms due to collisions or interactions between the flowing charge carriers and the lattice atoms, and therefore to an increase in its kinetic energy and consequently to an increase of the thermal energy (heating). The electrical energy of a DC impulse is dependent on the electrical power P and the pulse duration $\Delta t$:

$$E_{et} = F \cdot \Delta t$$

The thermal energy as well as the electrical energy is usually given with the units of Watt Seconds (Ws) or Joules (J).

When flowing through a piece of metal, the electrical energy is completely converted into thermal energy which leads to a thermal energy difference between before (t0) and after (t1). During the duration of the impulse the temperature difference between the section of the metal lattice through which current flows and adjacent structures leads to an outflow of thermal energy $E_{Diss}$ into the surroundings. This outflow is dependent on various material constants, which are bundled into the variable k and are not specified in greater detail, as well as on the integral of the temperature difference with respect to the time $\Delta t$:

$$E_{Diss} = k \cdot \int_{\Delta t} \Delta T(t) \cdot dt$$

The outflow of the thermal energy into the surroundings according to the above relationship has a strong dependence on the impulse duration $\Delta t$. That is, the shorter the pulse, the less thermal energy flows away.

The difference in the thermal energy between before (t0) and after (t1) can be described as follows:

$$E_{th,t1} = E_{th,t0} + E_{el} - E_{Diss}$$

The Temperature rise $\Delta T$ can be calculated as follows:

$$\Delta T = (T_{t1} - T_{t0}) = \frac{E_{el}}{c \cdot m} - E_{Diss}$$

With use of the mass density formula and separation of the material constants there results the following proportional relationship:

$$\Delta T = \frac{1}{c \cdot \rho} \cdot \frac{E_{el}}{V} - k \cdot \int_{\Delta t} \Delta T(t) \cdot dt$$

According to the above relationship one has thus three possibilities to increase the temperature rise in an implant material.
a) One increases the supplied electrical energy $E_{el}$
b) One reduces the volume V through which direct current flows
c) One reduces the impulse duration (in order to minimize the heat dissipation effect)

A reduction of the impulse duration according to point c) leads simultaneously to a reduction of the electric energy $E_{el}$ according to point a). However this may be compensated by an increase of the electrical power P. It is therefore appropriate to minimize the impulse duration $\Delta t$ (in order to minimize the heat dissipation during the energy input) and simultaneously to maximize the electrical power P (in order to deliver sufficient electrical energy $E_{el}$ despite lower impulse duration).

It is therefore provided according to the invention that the bipolar cutting instrument creates a local heating of a gripped piece of metal (with the aim of local melting), which heating is as strong as possible, while making a required input of electrical energy as small as possible. Here the gripped target metal should be melted while the instrument material should remain intact and the surrounding tissue should remain undamaged.

Heating Process, Influence of Material Constants

Figure 12:
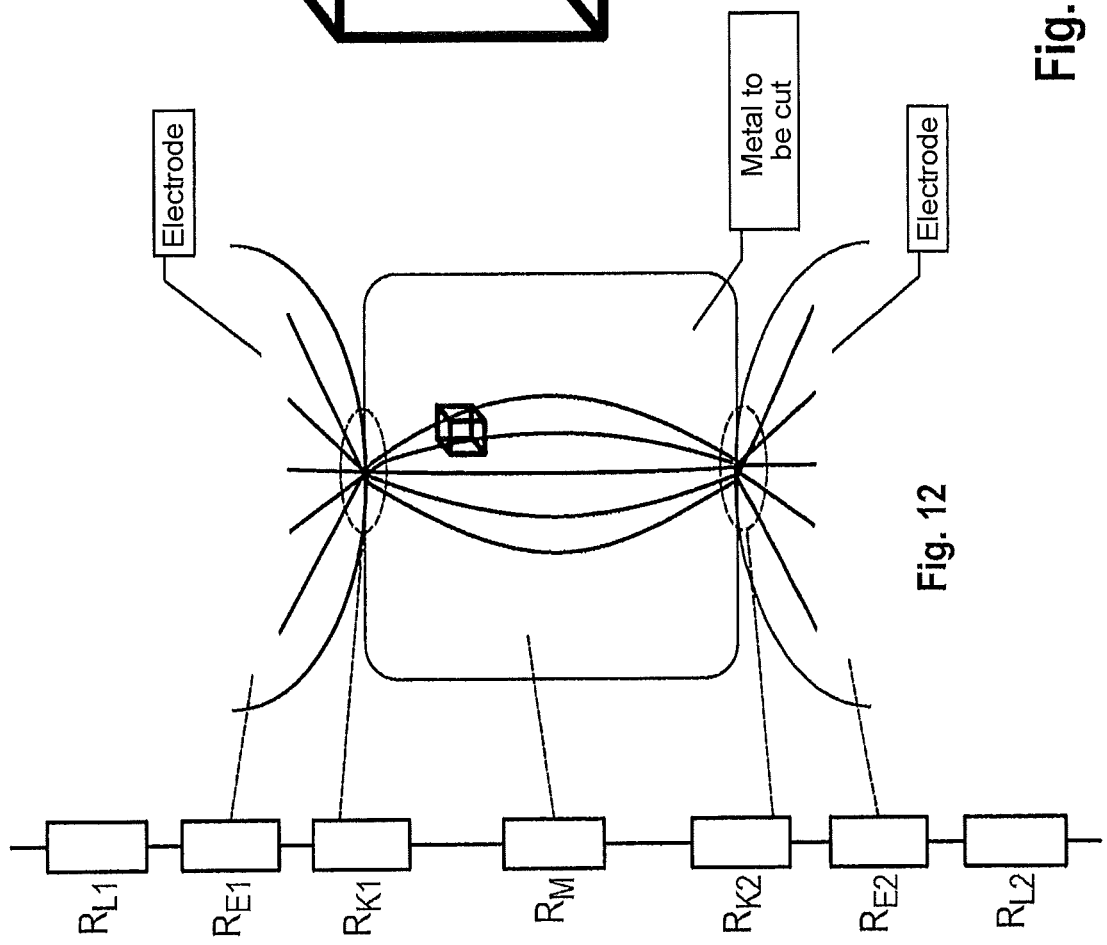
FIG. 12 shows the electrical current path according to FIG. 11 according to the current densities to be expected in individual path sections.
Figure 12:
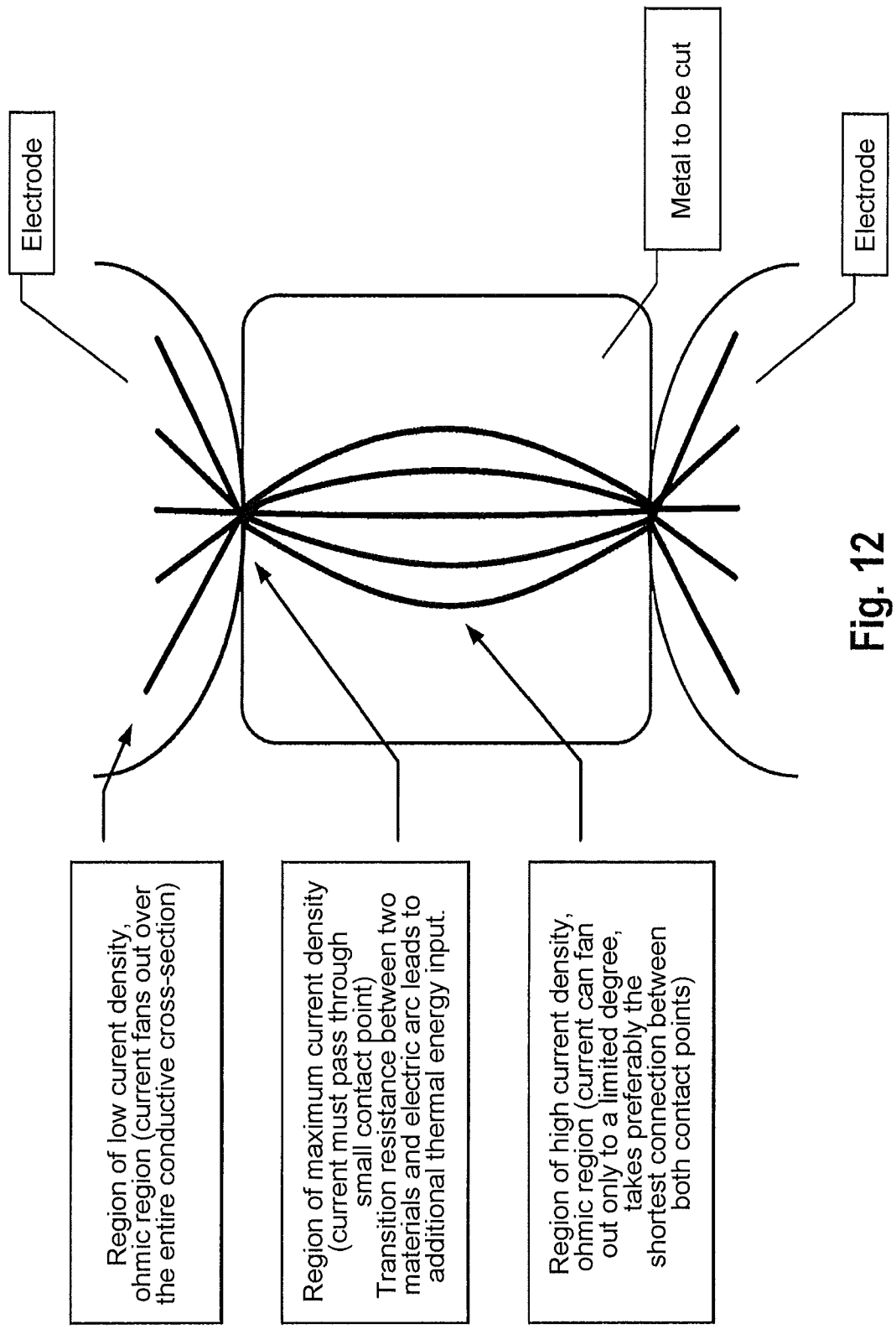

As is shown in FIG. 12, the cutting process is influenced on the one hand by material constants, and on the other hand by the geometric proportions relating to the current path and which in particular determine the current density.

Figure 11:
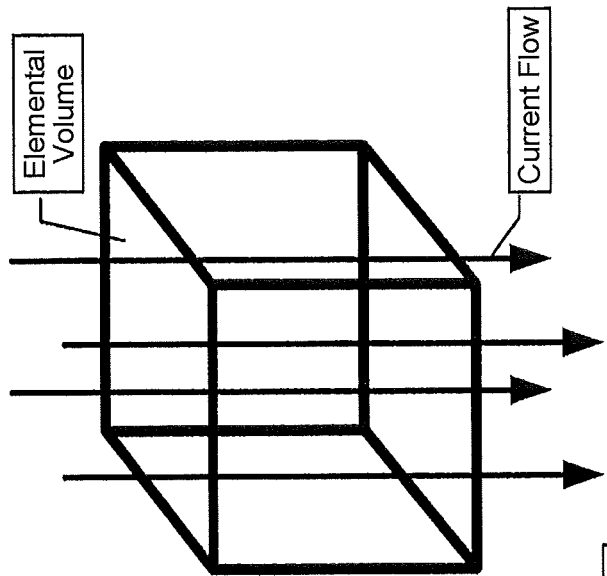
FIG. 11 shows the basic principle of an electrical current path through a metallic implant on which two opposite-lying electrodes are punctiformly applied.
Figure 13:
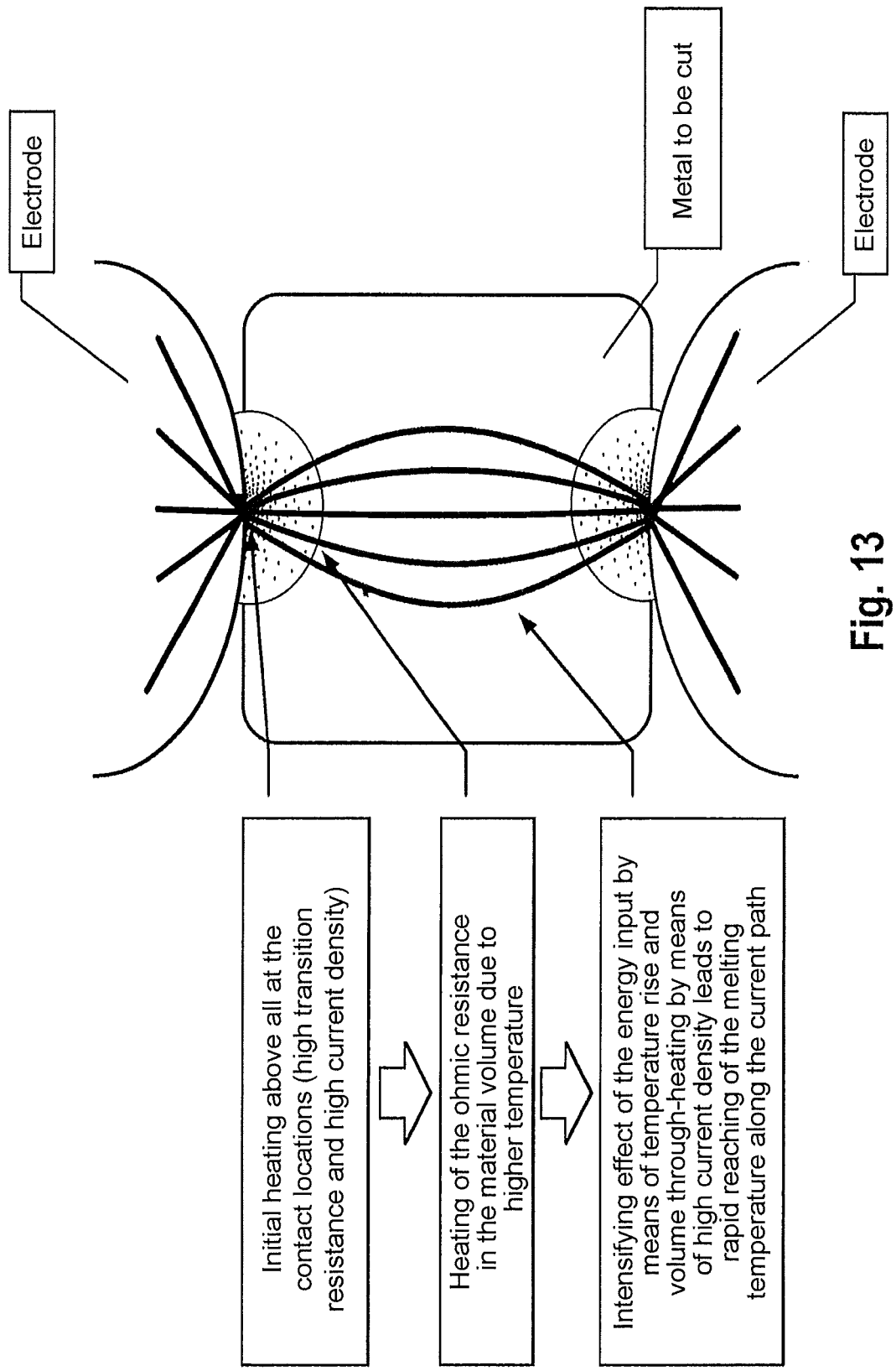

The melting of an elemental volume by electric direct current according to FIG. 13 may be calculated as follows:

The thermal energy $E_{th}$ that is necessary to melt an elemental volume according to FIG. 11 of a material is dependent on the start temperature $T_O$ of the melting temperature $T_S$, the specific heat capacity c as well as the specific weight (mass density) ρ:

$$E_{th} = \rho \cdot V \cdot (T_S - T_O)$$

$T_O = 38°$ C. (body temperature) and a standard volume of 1 mm$^3$ gives rise to values for the melting energy per mm$^3$ according to the following table (FIG. 14). The readiness of a material to convert electrical energy into thermal energy is proportional to the ohmic resistance of the material. In order to take this into account for the application case of the implant-cutting instrument according to the invention (whereby the same current flows through different materials), the specific melting energy is adjusted by the ohmic resistance (by multiplication with the reciprocal value of the resistance). This gives a measure on the basis of which a comparability of the materials with respect to their energy absorption characteristics and suitability for use in the current path is possible. So, for example, unalloyed steel is suited very well as an electrode material for cutting nickel-titanium because this measure (i.e. the specific melting energy adjusted by the resistance factor) for unalloyed steel, being 39, is distinctly higher than for nickel-titanium, being 4.86 (last column in FIG. 14). In other words when the same current flows through both materials, nickel-titanium melts faster than unalloyed steel by the ratio 39 to 4.86.

In conclusion a surgical implant-cutting instrument of the bipolar type, operated with direct current, is disclosed, with an instrument head which is located at the distal end of an instrument shank and which is provided for minimally invasive insertion of the instrument into a patient's body, wherein at least two mutually opposing instrument branches, preferably of the linear type, are arranged on the instrument head and between them define a cutting gap for receiving an electrically conductive implant or implant section between them. According to the invention electrodes are formed on the mutually facing longitudinal sides of the branches or these are each equipped with at least one electrode, which electrodes are in turn shaped at their mutually facing longitudinal sides to form a cutting edge in order to effect a quasi linear or punctiform physical contact engagement with the electrically conductive implant or implant section for an electrical short circuit of the mutually opposing electrodes.

Detection of Contact Quality

According to the invention it is provided to accomplish the melting of the target metal by means of a DC power current (in the range of approx. 100-150 amperes) via an endoscopic instrument. It is important here that the target metal of the implant is selectively melted, i.e. that the direct current melts the stent material but not the conductor/electrode material of the endoscopic surgical implant-cutting instrument. A suitable dose (setting) of current strength and impulse duration or impulse form is decisive for this purpose.

The term 'contact quality' is understood in this context to mean the conditions set for current density and current path length which arise when contacting of the implant material with the instrument. Influencing factors can for example be the concrete transformation of the gripped/contacted implant section. If the gripped/contacted implant section between the electrodes is thin and planar, there arises a small current density, but if it is narrow, there arises a high current density. The concrete contact situation can break down very differently in individual cases, such that different contact qualities result. In order to ensure a reliable cutting and at the same time to avoid an excessive energy input (which can lead to explosion effects or can damage the instrument), it is practical to adjust the current strength and impulse duration or impulse form.

The contact quality may be performed via a resistance measurement. The current path can be described, according to FIG. 7, via an equivalent circuit diagram with the following ohmic resistances arranged in series.

$R_{L1}$ Resistance of conductor 1
$R_{E1}$ Resistance of electrode 1
$R_{K1}$ Contact resistance (electrode 1-stent material) 1
$R_M$ Resistance of the metal to be cut
$R_{K2}$ Contact resistance (electrode 2-stent material) 2
$R_{E2}$ Resistance of electrode 2
$R_{L2}$ Resistance of conductor 2

The determination of contact quality occurs according to the principle of four-wire sensing. This is applied before the actual cutting process for the determination of appropriate cutting parameters (current strength, impulse duration and impulse form) as well as during the cutting process. The basic principle is shown in FIG. 8.

In an embodiment variant of the determination of contact quality a small test current is introduced into the instrument before the cutting process such that the test current flows via the electrodes through the stent material to be cut. The voltage drop $U_T$ between the two electrodes and created by the test current may be measured via two conductors which are in electrical contact with the electrodes but through which the test current does not flow. This corresponds to a measurement of the resistances $R_{E1}$, $R_{K1}$, $R_M$, $R_{K2}$ and $R_{E2}$ in the equivalent circuit diagram, according to the principle of four-wire sensing. The test current lies distinctly below the power current, preferably in the milliampere range (e.g. 20 mA). In addition to the determination of the contact quality it may also be determined whether an electrically conductive contact was made at all.

In a further embodiment variant of the determination of contact quality a test impulse is sent before the cutting process (preferably when a stable electrical contact has been established), through the implant material to be cut, which leads to heating but does not lead to melting. A heating leads to an increase in the specific resistance of the material and therefore to an increase in the voltage $U_T$ between the electrodes and determined according to the principle of the four-wire method. During this impulse a prognosis of the energy input required for melting may be computationally deduced based on the growth curves of the electrical resistance between the electrodes (which corresponds to the resistances $R_{E1}$, $R_{K1}$, $R_M$, $R_{K2}$ and $R_{E2}$ in the equivalent circuit diagram). This may serve as basis for the setting of the cutting parameters.

During the cutting process, the cutting process may be monitored from the monitoring of the voltage $U_T$ between the electrodes with the aim of adjusting the cutting parameters as necessary, such that e.g. a foreseeably too-low parameter setting is corrected.

Furthermore the voltages $U_{L1}$ and $U_{L2}$ are determined. This takes place not only with the test current before the cutting process but also with the power current during the cutting process. Since the ohmic resistance of the conductor material changes with temperature, the ohmic resistance, and with it the temperature, can be ascertained by measurement of the voltage drop in the case of known current. This is appropriate in particular in order to recognize and avoid overheating of the instrument shank, through suitable setting of the cutting parameters or cancellation of the cutting process. The temperature coefficient of various conductive materials is shown in FIG. 14.

Since the test current is preferably many times smaller than the power current, it is appropriate to be able to optionally electronically amplify the measurement of the voltages $U_T$, $U_{L1}$ and $U_{L2}$. A simplified suitable circuit is shown in FIG. 9.

The invention claimed is:

1. A surgical implant-cutting instrument of bipolar type, operating on direct current, the implant-cutting instrument comprising: an instrument head on which at least two mutually opposing instrument branches are arranged which between them define a cutting gap extending in a longitudinal direction of the implant-cutting instrument, for receiving therebetween an electrically conductive implant or implant section; a current control device; and an electric/electronic contact quality detection device, wherein mutually facing longitudinal sides of the at least two mutually opposing instrument branches each form an electrode or are each equipped with at least one electrode, wherein at least one electrode is spherical cap-shaped so that the electrodes achieve at their mutually facing sides a punctiform contact, wherein the current control device is configured to apply to the electrodes a DC cutting current comprising a direct current of predetermined or adjustable current strength in a pulsed or timed way such that a quantity of current in at least one current pulse or cutting impulse is sufficient to melt, from the outside, a wire portion of the implant in contact between the electrodes at locations where the electrodes and the wire portion of the implant contact each other, and wherein the electric/electronic contact quality detection device is configured to perform a contact-quality detection test sequence prior to a cutting operation of the instrument and chronologically before application of the DC cutting current to the electrodes, or separately and independently from the cutting operation, the contact-quality detection test sequence providing an application to the electrodes of a test current below the DC cutting current, or an application to the electrodes of the DC cutting current but with a test impulse duration below a duration of the at least one current pulse or cutting impulse, in each case in order to determine a contact resistance between the electrodes and the implant or implant section, according to a principle of four-conductor-measurement.

2. The implant-cutting instrument according to claim 1, wherein a pulse width and/or the current strength is set or is settable via the current control device for obtaining a required quantity of current.

3. The implant-cutting instrument according to claim 1, wherein the electrodes are each shaped at their mutually facing sides to form a spherical cap whereby contact arises when the electrodes are brought together, in order to effect a punctiform physical contact engagement with the electrically conductive implant or implant section to be introduced therebetween, for an electrical short circuit of the mutually opposing electrodes.

4. The implant-cutting instrument according to claim 1, wherein DC current impulses of predetermined current strengths of up to 200 amperes are applied in a time period smaller than one second and in a controlled manner to the electrodes between which the cutting gap is formed in the longitudinal direction of the instrument.

5. The implant-cutting instrument according to claim 1, wherein a voltage lies below a limit of 48 Volts for a low voltage.

6. The implant-cutting instrument according to claim 1, wherein the at least two mutually opposing instrument branches are rigidly fixed to the instrument head.

7. The implant-cutting instrument according to claim 1, further comprising an actuating mechanism configured to move or set the at least two mutually opposing instrument branches to change a cutting gap width in a defined way.

8. The implant-cutting instrument according to claim 1, wherein the at least two electrodes and/or the at least two mutually opposing instrument branches are oriented with respect to each other to be essentially V-shaped so that the cutting gap formed therebetween narrows in a proximal direction, continuously or in a convex curve shape.

9. The implant-cutting instrument according to claim 1, further comprising a biasing device provided at the instrument head, the biasing device being configured to bias the electrodes and/or the instrument branches against each other with a predetermined biasing force so that an implant material is introduced therebetween in an insertion process and is automatically compressed or crushed by the insertion process itself.

10. The implant-cutting instrument according to claim 1, wherein in a case of falling below a threshold value the electric/electronic contact quality detection device is configured to output a warning signal and/or block a subsequent application of the DC cutting current.

11. The implant-cutting instrument according to claim 1, wherein the electric/electronic contact quality detection device is configured to adjust the amount of the DC cutting current to be supplied for the cutting operation correspondingly to the contact resistance between the electrodes and the implant or implant section that is determined by the contact-quality detection test sequence.

12. The implant-cutting instrument according claim 1, wherein the electric/electronic contact quality detection device is configured to verify in the contact quality detection test sequence whether the DC cutting current required for melting of the implant or implant section brings about a heating of the implant-cutting instrument below a thermal load capacity of supply lines and/or of the electrodes.

13. The implant-cutting instrument according to claim 1, wherein the at least two mutually opposing instrument branches or the electrodes are made from a heat resistant material whose resistance-adjusted specific melting energy is larger than $5.99 \cdot 10^{15}$ J m$^{-4}$Ω$^{-1}$.

14. The implant-cutting instrument according to claim 1, wherein the at least two mutually opposing instrument branches or electrodes mounted to them are configured springily resiliently.

15. The implant-cutting instrument according to claim 1, wherein the at least two mutually opposing instrument branches or the electrodes mounted to them are mounted at the instrument head for an automatic setting of gap width such that implants of different material thicknesses can be introduced into the cutting gap for a short-circuit of the electrodes.

16. The implant-cutting instrument according to claim 1, wherein in a case of reaching or exceeding a threshold value, the electric/electronic contact quality detection device is configured to output an acceptance signal and/or permit a subsequent application of the DC cutting current.

17. A surgical implant-cutting instrument of bipolar type, operating on direct current and comprising: an instrument head on which at least two mutually opposing instrument branches are arranged to define a cutting gap between the at least two instrument branches and extending in a longitudinal direction of the instrument, the cutting gap being configured to receive an electrically conductive implant or implant section, wherein mutually facing longitudinal sides of the at least two mutually opposing instrument branches each form an electrode or are each equipped with at least one electrode, the electrodes being shaped so that they achieve at their mutually facing sides a punctiform contact or an essentially one-dimensional linear contact extending in a longitudinal direction of the electrodes, a current control device configured to apply to the electrodes a DC cutting current comprising a direct current of predetermined or adjustable current strength in a pulsed or timed way such that a quantity of current in at least one current pulse or cutting impulse is sufficient to melt, from the outside, a wire portion of the implant in contact between the electrodes, at locations where the electrodes and the wire portion of the implant contact each other, and an electric/electronic contact quality detection device configured to perform a contact-quality detection test sequence in the event of a cutting operation of the instrument and chronologically before the resulting application of the DC cutting current to the electrodes, or separately and independently from the cutting operation, wherein the contact-quality detection test sequence provides an application to the electrodes of a test current below the DC cutting current, or an application to the electrodes of the DC cutting current but with a test impulse duration below a duration of the at least one current pulse or cutting impulse, in each case in order to determine a contact resistance between the electrodes and the implant or implant section, according to a principle of four-conductor-measurement.

18. The surgical implant-cutting instrument according to claim 17, wherein the electric/electronic contact quality detection device is configured to verify in the contact quality detection test sequence whether the DC cutting current required for melting of the implant or implant section brings about a heating of the implant-cutting instrument below a thermal load capacity of supply lines and/or of the electrodes.

* * * * *